United States Patent [19]
Brüggemann et al.

[11] Patent Number: 5,892,058
[45] Date of Patent: Apr. 6, 1999

[54] HYDROXYMETHYLATION OF TOCOPHEROLS

[75] Inventors: Konrad Brüggemann, Wallbach, Switzerland; Juan Ramon Herguijuela, Auggen, Germany; Thomas Netscher, Bad Krozingen, Germany; Johann Riegl, Freiburg, Germany

[73] Assignee: Roche vitamins Inc., Parsippany, N.J.

[21] Appl. No.: 848,041

[22] Filed: Apr. 28, 1997

Related U.S. Application Data

[63] Continuation of Ser. No. 729,967, Oct. 15, 1996, abandoned.

[30] Foreign Application Priority Data

Oct. 18, 1995 [CH] Switzerland ............... 2951/95

[51] Int. Cl.$^6$ ................................. C07D 311/04
[52] U.S. Cl. ........................................... 549/412
[58] Field of Search ............................. 549/412

[56] References Cited

U.S. PATENT DOCUMENTS 3,338,922  8/1967  Kijima et al. .
3,819,657  6/1974  Baldwin et al. .

FOREIGN PATENT DOCUMENTS 178 400   4/1986   European Pat. Off. .
191 132   8/1986   European Pat. Off. .
60-4183   2/1985   Japan .

Primary Examiner—Johann Richter
Assistant Examiner—Taofiq A. Solola
Attorney, Agent, or Firm—George W. Johnston; Dennis P. Tramaloni; Bruce A. Pokras

[57] ABSTRACT

A method of producing α-tocopherol from non-α-tocopherols is disclosed. In the disclosed method, non-α-tocopherols are hydroxymethylated and reduced to α-tocopherol in a single step by reacting formaldehyde or a formaldehyde-producing compound with the non-α-tocopherol under catalytic reducing conditions in a reaction mixture containing the non-α-tocopherol, formaldehyde or formaldehyde-producing compound and boric acid or a boric acid-producing compound dispersed in a solvent of an azeotropic mixture of trimethyl borate and methanol and a non-polar organic solvent.

9 Claims, 2 Drawing Sheets

HYDROXYMETHYLATION OF TOCOPHEROLS

This is a continuation of application Ser. No. 08/729,967, filed Oct. 15, 1996, now abandoned.

BACKGROUND OF THE INVENTION

The present invention is concerned with the hydroxymethylation of mixtures containing so-called "non-α-tocopherols" and the subsequent conversion of the hydroxymethylation products into α-tocopherol, with the two reaction steps being carried out together as a one-pot process.

As is known, the naturally occurring non-α-tocopherols, β-, γ- and δ-tocopherol, differ from α-tocopherol, the tocopherol which has the highest vitamin E activity and which is therefore the biologically most valuable tocopherol, by the absence of one or two methyl groups in the 5- and/or 7-position of the chroman part of the molecule. Accordingly, there exists a need for the chemical conversion of such non-α-tocopherols into (α-tocopherol, with the main problem residing in the efficient, complete mono- or dimethylation of the benzene ring of the substituted chromanyl group.

Since synthetic processes for the manufacture of α-tocopherol identical to the natural form thereof have hitherto been found to be uneconomical, and natural, especially vegetable, sources of tocopherols usually contain only a relatively small amount of α-tocopherol, but predominantly non-α-tocopherols, such that the isolation of α-tocopherol from such natural materials (raw materials) is also not particularly viable, the object of the present invention is to develop a process for the conversion of non-α-tocopherols, which may be present in respective raw materials or obtainable therefrom, into α-tocopherol, this process being more economical in many respects than previous pertinent processes.

With the same purpose as the object of the present invention, several processes for the conversion of non-α-tocopherols into α-tocopherol are known from the state of the art. For example, Japanese Patent Publication (Kokoku) No. 4183/1985 (Eisai Co. Ltd.) discloses a process for the manufacture of α-tocopherol from non-α-tocopherols by reacting at least one non-α-tocopherol with formaldehyde in the presence of boric acid or a derivative thereof under catalytic reducing conditions. This process, which comprises not only hydroxymethylation but also a subsequent reduction, is a one-pot process, so that the isolation of the very unstable hydroxy-methylated intermediates as well as side-reactions are avoided.

However, the process is clearly carried out at relatively high temperatures of about 200° C. (see Examples 1–12), which is known to lead to an undesired decomposition of the formaldehyde to carbon monoxide and hydrogen and consequentially to a pressure increase in the reaction vessel. Further, it is noted that a whole series of allegedly suitable solvents, inter alia also the reagent "alkyl borate" (trialkyl borate, e.g., trimethyl borate), is mentioned; but the possibility of using a combination of solvents is not suggested. In view of the use of relatively high temperatures in the known process, this necessitates stronger and consequently more expensive process equipment (autoclaves) as well as high energy costs for the heating and cooling. In particular, the pressure increase caused by the decomposition of the formaldehyde gives rise to problems, not least dangers, in carrying out the reaction: the gases thereby generated necessitate expensive safety measures, which reduces the economy and renders additional investments necessary.

Further, the best results are achieved when trimethyl borate is used as the single solvent. This use, however, is expensive in the production or recycling and accordingly represents an expensive measure. Therefore, the process disclosed in Japanese Patent Publication No. 4183/1985 has serious disadvantages with respect to plant investment and operating costs.

SUMMARY OF THE INVENTION

It has now surprisingly been found that this known process of Eisai Co. Ltd. can be improved decisively by a very particular choice of reaction conditions. The object of the present invention is a process for the conversion of non-α-tocopherols into α-tocopherols by reacting (hydroxymethylating) at least one non-α-tocopherol with formaldehyde or a formaldehyde-producing compound in the presence of boric acid or a boric acid-producing compound under catalytic reducing conditions at a temperature in the range from about 130° C. to about 180° C., wherein the reaction is carried out with the reactants dispersed in a solvent comprising an azeotropic mixture of trimethyl borate and methanol and a non-polar organic solvent.

DETAILED DESCRIPTION OF THE INVENTION

Figure 1:
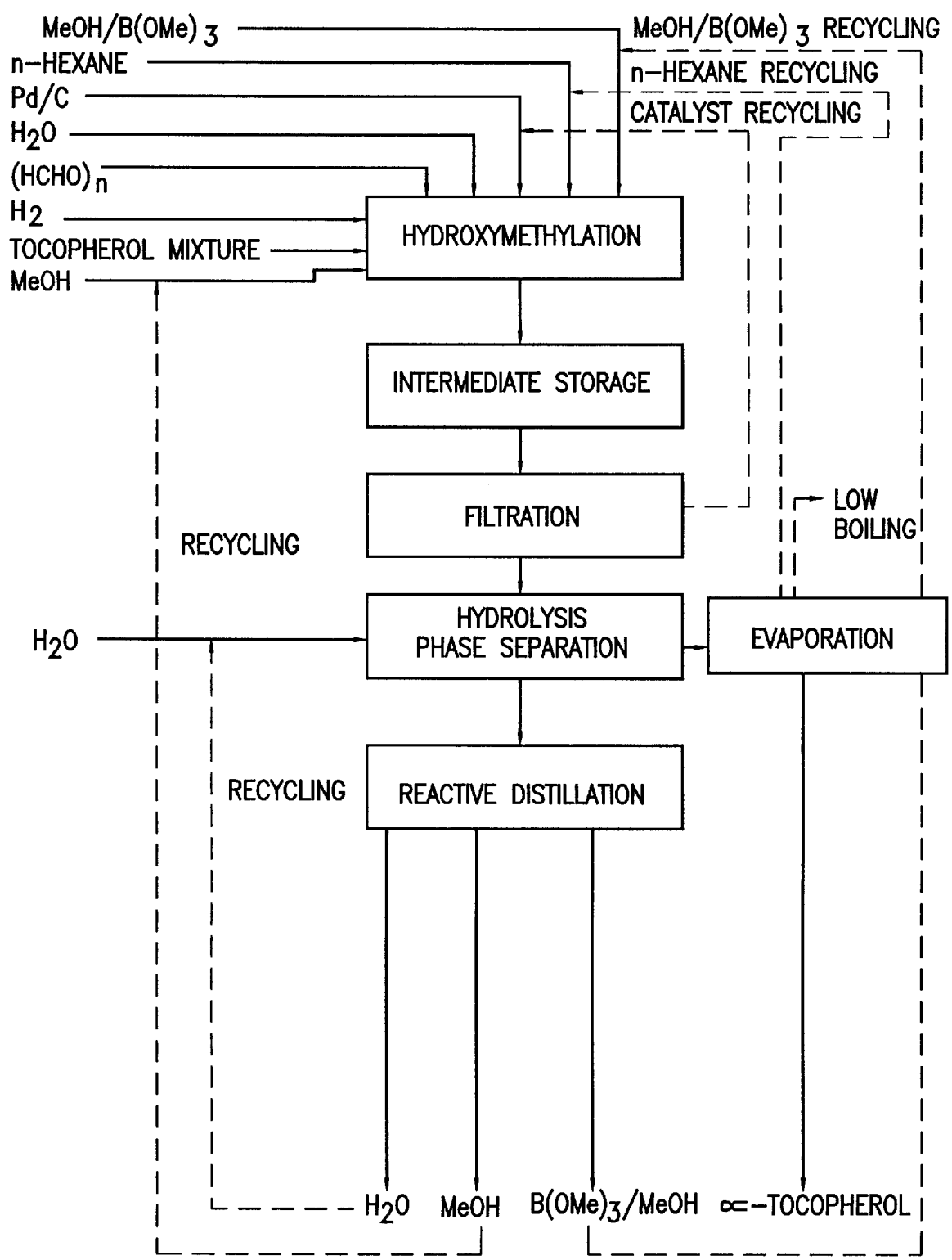
FIG. 1: A schematic of the manufacturing process, the working-up, the recovery of the process components and their recycling for a new batch.

We have discovered a process for producing α-tocopherol from a non-α-tocopherol, wherein the non-α-tocopherol is free of or combined with α-tocopherol, which process comprises reacting the non-α-tocopherol with formaldehyde or formaldehyde-producing compound in a reaction mixture which further comprises boric acid or a boric acid-producing compound and a solvent comprising an azeotropic mixture of trimethyl borate and methanol and a non-polar organic solvent wherein:

said reaction is carried out under catalytic reducing conditions at a temperature in the range from about 130° C. to about 180° C.; and the mol equivalent ratio of formaldehyde to non-α-tocopherol is in a range from about 2:1 to about 10:1, the mol equivalent ratio of boric acid to total non-α-tocopherol and α-tocopherol is in a range from about 0.1:1 to about 4:1, the mol equivalent ratio of trimethyl borate to total non-α-tocopherol and α-tocopherol is in a range from about 0.1:1 to about 10:1, and the ratio of liters of non-polar organic solvent per mol equivalent of total non-α-tocopherol and α-tocopherol is in a range from about 1:1 to about 10:1;

so that the non-α-tocopherol is reacted to produce the α-tocopherol.

As indicated earlier, a raw material which contains at least one non-α-tocopherol, e.g., β-, γ- or δ-tocopherol, or a tocopherol mixture, which is produced or otherwise obtained from such a raw material and which likewise contains at least one non-α-tocopherol, can in principle be used as the educt in the process in accordance with the invention. Since, as is known, vegetable oils and fats such as, for example, soya oil, rape oil, cotton seed oil, groundnut oil, wheatgerm oil, corn oil, barley oil, rye oil, thistle oil and the like are valuable natural sources of tocopherols (including α- and non-α-tocopherols), such oils or preferably their distillates, which have a higher content of tocopherols and contain less undesired accompanying components, e.g., sterols, free and esterified fatty acids, waxes and glycerides, can be used as the educt in the process in accordance with the invention. In particular, thistle oil and soya oil have been found to be valuable sources of tocopherols, including α-tocopherol and the non-α-tocopherols which are to be converted into α-tocopherol in accordance with the invention. Of course, it is unimportant whether, inter alia, α-tocopherol itself is present in the educt, since the α-tocopherol does not prevent the conversion of the non-α-tocopherols into α-tocopherol and itself remains unchanged by the process of the invention.

The term "formaldehyde-producing compound" includes any conventional compound which can act as a source of formaldehyde under the conditions of the process of the invention. Preferred formaldehyde-producing compounds which can be used in accordance with the present invention are an oligomer of formaldehyde, such as, for example, paraformaldehyde, or a formaldehyde addition product which yields formaldehyde on cleavage, such as, for example, formaldehyde dimethyl acetal. If desired, the formaldehyde can be used as gaseous formaldehyde. However, solid paraformaldehyde is preferably used. The amount of formaldehyde (as such or as part of the formaldehyde-producing compound) which is used suitably lies between about 2 and 10 mol equivalents, preferably between about 4 and about 8 mol equivalents, per mol equivalent of non-α-tocopherol.

A further feature of the process in accordance with the invention comprises carrying out the hydroxymethylation in the presence of boric acid or a boric acid-producing compound. In the latter case an especially suitable boric acid-producing compound is trimethyl borate, which is in any event present in the reaction mixture as a component of the solvent, wherein the reaction mixture further comprises water in order to generate boric acid in situ from the trimethyl borate. Where boric acid itself is used, then its amount is suitably about 0.1 to about 4 mol equivalents, preferably about 0.5 to about 1 mol equivalent, per mol equivalent of total α-tocopherol and non-α-tocopherol (total tocopherols). When the already present trimethyl borate together with added water is employed as the source of boric acid, about 0.3 to about 12 mol equivalents, preferably about 1.5 to about 3 mol equivalents, of water are preferably added to the reaction mixture per mol equivalent of total tocopherols. The process of the invention is preferably carried out using in situ generated boric acid.

Further, the hydroxymethylation is carried out under catalytic reducing conditions. This means that the process of the invention is carried out under conditions which are sufficient to reduce, i.e., hydrogenate, the hydroxymethylated non-α-tocopherol which is formed by the reaction of the non-α-tocopherol with the formaldehyde or a formaldehyde-producing compound, in order to produce the α-tocopherol. Thus, the hydrogenation of the hydroxymethylated tocopherol or tocopherol mixture is carried out in the same reaction vessel as used for the hydroxymethylation without the necessity of isolating the hydroxymethylated product.

Any conventional catalytic reducing conditions may be used in accordance with the present invention. Preferably a conventional noble metal catalyst, e.g., a palladium- or platinum-based hydrogenation catalyst is present in the reaction mixture in a sufficient quantity to catalyze the hydrogenation of the hydroxymethylated non-α-tocopherol to α-tocopherol. Palladium on active charcoal is preferably used as the noble metal catalyst for the hydrogenation. Palladium on active charcoal with a 5 to 10% palladium content is the most preferred catalyst. Any hydrogen pressure sufficient to carry out the hydrogenation of the non-α-tocopherol to α-tocopherol may be utilized in accordance with the invention. The hydrogenation is preferably carried out under a hydrogen pressure in a range from about 10 bar to about 75 bar, more preferably under a pressure in a range from about 25 bar to about 35 bar.

The "azeotropic" mixture of trimethyl borate and methanol, which is used in the process in accordance with the invention as a component of the solvent, has by necessity a certain weight ratio. This ratio (trimethyl borate:methanol) preferably lies in the proximity of the azeotrope, i.e., at about 50:50 to about 75:25, more preferably about 70:30. Based on the amount of total non-α-tocopherol and α-tocopherol employed, the mol equivalent ratio trimethylborate:total tocopherols should be in a range from about 0.1:1 to about 10:1, preferably about 1:1 to about 4:1.

An additional solvent, namely a non-polar organic solvent, is also used in accordance with the process of the invention. This solvent is preferably a lower (especially $C_{5-8}$) alkane, a mixture of alkanes (e.g., petroleum ether) or an aromatic hydrocarbon, e.g., toluene. The use of a lower alkane, especially n-hexane, is particularly preferred. From about 1 litre to about 10 litres, preferably about 1 to 3 litres, of the non-polar organic solvent, are used per mol equivalent of total tocopherols.

In principle, the process in accordance with the invention is carried out by placing the aforementioned starting raw material or tocopherol mixture, the formaldehyde or the formaldehyde-producing compound, the solvent (azeotropic mixture of trimethyl borate and methanol as well as non-polar organic solvent), the boric acid or the water as well as the hydrogenation catalyst in the reaction vessel and introducing hydrogen until the hydrogenation pressure has been reached. Then, the reaction mixture is heated, preferably while stirring.

Any temperature sufficient to carry out the hydroxymethylation and hydrogenation of the present process may be used so long as it is below the temperature where significant formaldehyde decomposition will occur (e.g., 200° C.). The reaction is preferably carried out at temperatures in a range from about 130° C. and about 180° C., more preferably in a range from about 140° C. and about 170° C. The reaction is carried out for sufficient time to provide the desired yield of α-tocopherol, generally between 4 and 8 hours. The course of the reaction can be followed using chromatographic methods, e.g., gas chromatography (GC), and, after complete reaction has been established, the resultant α-tocopherol, which as a rule is free from non-α-tocopherol homologues β-, γ-, δ-tocopherol), can be isolated, if desired, from the mixture remaining according to methods known per se and then purified if required. Also, inter alia, the catalyst can be re-used, for example after rinsing with a suitable organic solvent, e.g., methanol.

The present invention includes as a further aspect the working up of the mixture after completion of the reaction, this comprising not only the isolation of the α-tocopherol, but also an almost complete separation of all solvent components used in the reaction, of the catalyst and, when boric acid is used, of this or of the trimethyl borate, so that the recovered substances can be used again (recycled). The working up is economical and therefore advantageous.

It is characteristic of the working up that the recovery of the boric acid or of the trimethyl borate is effected solely in the form of a trimethyl borate-methanol mixture by rectificative distillation. As mentioned earlier, the boric acid required for the reaction which takes place in the process in accordance with the invention can be added as such or can be generated in situ from the trimethyl borate present in the reaction mixture (as part of the azeotropic mixture) by the addition of water.

The working up comprises treating the mixture remaining after completion of the reaction with methanol, whereby the boric acid dissolves in the methanol, filtering off the thus-obtained remaining solution, supplemented if desired by non-polar organic solvent rinsings, from the solid catalyst, which can be isolated in this way and reused, treating the (total) filtrate with water, after phase separation distillatively removing the non-polar organic solvent from the organic phase in order to liberate the α-tocopherol reaction product, and subjecting the aqueous phase, which comprises mainly methanol, water and boric acid, to a so-called reactive distillation in order to separate the trimethyl borate, produced in the distillation as a result of the esterification of boric acid with methanol, as an "azeotropic" mixture of trimethyl borate and methanol, and in addition recycling the methanol and water.

Since, as is known, boric acid alkyl esters are hydrolyzed very readily, it is surprising that "azeotropic" mixtures of trimethyl borate and methanol can be obtained from mixtures of boric acid, water and methanol having a water content of over 30%. Using this working up procedure, the reaction product, consisting mainly of α-tocopherol, can be isolated and the methanol, the water, the non-polar organic solvent, the hydrogenation catalyst as well as the boric acid can be isolated as an "azeotropic" mixture of trimethyl borate and methanol and used again (recycled).

The solvent combination of the (commercially available) azeotropic mixture of trimethyl borate and methanol with a nonpolar organic solvent, preferably with n-hexane, used in the process in accordance with the invention permits, in comparison to the state of the art, clearly more favourable reaction conditions with just as high yields of α-tocopherol. This result is therefore surprising, because the results cannot be achieved using each solvent individually, in that, for example, poorer conversion or increased byproduct formation occur, or a necessarily higher reaction temperature is needed if the solvent combination of the present invention is not used. From this there result, inter alia, the following economically useful advantages of the process in accordance with the invention:

1) By virtue of the lower reaction temperature:
   less decomposition of formaldehyde, and consequentially less formaldehyde consumption, simplified reaction procedure [for example, as a consequence of no (excessive) pressure increase] and avoidance of additional expensive safety precautions;
   cost-effective processing plant and lower energy costs, i.e. lower investment and operating costs;
   more rapid heating and cooling phases during performance of the process; as well as
   less thermal damage to educt and product (tocopherols).
2) By virtue of the use of the azeotropic mixture:
   lower operating costs by virtue of the usability of the substantially cheaper azeotropic mixture of trimethyl borate and methanol compared with trimethyl borate;
   avoidance (to a large extent) or the handling of solid boric acid, which permits a cost-effective process, as well as absolutely continuous recycling of the boron reagents (in the case of reactive distillation) and solvents, which again permits a cost-effective (economically performable) process.

The present invention is illustrated by the following Examples:

EXAMPLE 1

Hydroxymethylation-hydrogenation of δ-tocopherol (one pot process)

25.75 g of d-δ-tocopherol [from Sigma; about 90%, δ-tocopherol content 84.6%, 54.1 mmol; γ-tocopherol 5.3%, 3.3 mmol; α-tocopherol 1.3%, 0.8 mmol; total tocopherols 91.2%, 58.2 mmol; determined by GC of the acetates, internal standard squalane; stereochemical purity: >99.5% R,R,R-isomer (HPLC of the methyl ether derivative, determined on Chiracel OD, a commercially available chromatography (HPLC) column from Daicel)], 80 ml of n-hexane, 35.4 g of trimethyl borate-methanol azeotrope (trimethyl borate content 70 wt.%, corresponding to 24.8 g of trimethyl borate), 14.0 g of paraformaldehyde (corresponding to 466 mmol, 8 mol equivalents, based on total tocopherols), 1.57 ml of water (low in ions, 87.2 mmol, for the production of 29.1 mmol of boric acid, 0.5 mol equivalent based on total tocopherols) and 2.5 g of palladium on active charcoal (10%, Degussa E10N/D) are placed together in a 500 ml steel stirring autoclave having a mechanical gasification stirrer.

After closure the autoclave is, without stirring, flushed by three-fold pressurization to about 10 bar of hydrogen, with pressure subsequently being released. It is then pressurized to 15 bar of hydrogen while stirring at 22° C. It is heated to 161° C. for about 15 minutes while stirring (300 r/min.). The pressure thereby rises to 26.6 bar. Further hydrogen is introduced until the pressure is 30 bar and the mixture is stirred for 7 hours at 159 to 160° C. and with an open hydrogen valve, with the pressure being regulated between 29.7 and 31.3 bar. The mixture is left to cool to 20° C. for one hour.

After opening the autoclave the reaction mixture is separated from the catalyst over a frit and the solid residue (catalyst and boric acid) is washed three times with 100 ml of n-hexane each time (when it is desired to recycle the boric acid by reactive distillation in accordance with Example 4 the residue is also washed with methanol). The organic filtrates are combined and freed from the readily volatile components under reduced pressure of 400 mbar and at a bath temperature of 60° C. The resulting red-brown, clear, often slightly turbid distillation residue is taken up in 250 ml of n-hexane and the mixture is stirred for 30 minutes at 55–60° C. in a 500 ml round flask with 150 ml of water as a two-phase mixture. Hydrolysis of the boric ester thereby takes place. The hexane phase is washed once with 150 ml of water in a 500 ml separating funnel in order to remove the boric acid and the hexane phase is separated and dried over 3 g of anhydrous magnesium sulphate for 10 minutes while stirring.

After filtration and distillation of the solvent at 400 mbar and a bath temperature of 60° C. and subsequent drying for 30 minutes at 15 mbar and a bath temperature of 60–70° C. there are obtained 28.62 g of crude α-tocopherol as a yellow to light brown oil; α-tocopherol content (GC of the acetates, internal standard squalane) 81.5%, chemical yield α-tocopherol) 93.1%, no other homologues (β-, γ-, δ-tocopherol), 7-hydroxymethyl-β-tocopherol 1.6%, boron content <10 ppm. The solvent which is distilled off from the organic phase consists predominantly of n-hexane and can be immediately recycled. The combined aqueous phases contain methanol, water and boric acid and can be subjected to a distillative working up (see Example 4).

The crude α-tocopherol is treated with 25.0 g of acetic anhydride (corresponding to 244.9 mmol), 25.0 g of pyridine (corresponding to 316.1 mmol) and 1.0 g of 4-dimethyl-aminopyridine (corresponding to 8.2 mmol; catalytic amount) and stirred for one hour at room temperature. The reaction mixture is poured on to 100 g of ice/water (about 1:1), stirred for 30 minutes, treated with 250 ml of n-hexane and washed in succession twice with 150 ml of water each time, twice with 100 ml of 2N sulphuric acid each time, with 150 ml of water, with 150 ml of saturated sodium bicarbonate solution and three times with 150 ml of water each time. Thereafter, the mixture is dried over 3 g of anhydrous magnesium sulphate for 10 minutes while stirring. After filtration, distillation of the solvent at 400 mbar and a bath temperature of 60° C. and subsequent drying for 30 minutes at 15 mbar and a bath temperature of 70° C. there are obtained 29.26 g of α-tocopherol acetate as a yellow oil, α-tocopherol acetate content (GC, internal standard squalane) 87.5%, chemical yield (α-tocopherol acetate) 93.1%. This crude acetate is distilled in a bulb tube oven (250° C./10$^{-1}$ mbar). There are obtained 26.25 g of α-tocopherol acetate as a slightly yellowish oil which crystallizes slowly upon standing at room temperature. α-Tocopherol acetate content (GC, internal standard squalane) 96.2%, chemical yield 91.8%; stereo-chemical purity: 99.6% R,R,R-α isomer (HPLC of the methyl ether derivative on Chiracel OD, n-hexane); the product is identical with α-tocopheryl acetate according to $^1$H-NMR, IR, MS and microanalytical data.

EXAMPLE 2

Hydroxymethylation-hydrogenation of a tocopherol mixture (one pot process)

25.75 g of a tocopherol mixture from natural sources (consisting of α-tocopherol 3.9%, 2.3 mmol; β-tocopherol 1.0%, 0.6 mmol; γ-tocopherol 60.6%, 37.5 mmol; δ-tocopherol 26.4%, 16.9 mmol; total tocopherols 91.9%, 57.3 mmol; determined by GC of the acetates, internal standard squalane), 80 ml of n-hexane, 34.9 g of trimethyl borate-methanol azeotrope (trimethyl borate content 70 wt. %, corresponding to 24.4 g of trimethyl borate), 10.3 g of paraformadehyde (corresponding to 344 mmol, 6 mol equivalents, based on total tocopherols), 1.57 ml of water (low in ions, 87.2 mmol, for the production of 29.1 mmol of boric acid, 0.5 mol equivalent based on total tocopherols) and 2.5 g of palladium on active charcoal (10%, Degussa E10N/D) are placed together in a 500 ml steel stirring autoclave having a mechanical gasification stirrer.

After closure the autoclave is, without stirring, flushed by three-fold pressurization to about 10 bar of hydrogen, with the pressure being released each time. It is then pressurized to 15 bar of hydrogen while stirring at 22° C. It is heated to 163° C. for about 15 minutes while stirring (300 r/min.). The pressure thereby rises to 27.5 bar. Further hydrogen is introduced until the pressure is 30 bar and the mixture is stirred for 7 hours at 159–160° C. and with an open hydrogen valve, with the pressure being regulated at between 29.6 and 32.2 bar. The mixture is left to cool to 50° C. for one hour, the hydrogen is replaced by nitrogen, the autoclave is opened and 100 ml of methanol are added to the reaction mixture while stirring. The autoclave is again closed, stirred at 50° C. for minutes and then left to cool to 23° C. for 45 minutes.

After opening the autoclave the reaction mixture is separated from the catalyst over a frit and the solid residue (catalyst) is washed three times with 100 ml of n-hexane each time. The combined filtrates form a two-phase mixture. All readily volatile components are distilled off under reduced pressure of 400 mbar and at a bath temperature of 60° C. The yellow to light brown distillation residue contains small amounts of crystalline boric acid. The residue is taken up in 250 ml of n-hexane and the mixture is washed twice with 150 ml of water each time in a 500 ml separating funnel, with the boric acid being removed. The hexane phase is separated and dried over 3 g of anhydrous magnesium sulphate for 10 minutes while stirring.

After filtration and distillation of the solvent at 400 mbar and at a bath temperature of 60° C. and subsequent drying for 30 minutes at 15 mbar and a bath temperature of 60–70° C. there are obtained 26.91 g of crude α-tocopherol as a yellow to light brown oil; α-tocopherol content (GC of the acetates, internal standard squalane) 88.45%, chemical yield α-tocopherol) 96.5%, no other homologues (β-, γ-, δ-tocopherol), 7-hydroxymethyl-β-tocopherol 0.6%, boron content 11 ppm. If desired, the solvent and reagents can be recycled as described in Example 1.

The crude α-tocopherol is acetylated analogously to Example 1 to give 29.89 g of crude α-tocopheryl acetate as a yellow oil; α-tocopheryl acetate content (GC, internal standard squalane) 87.1%, chemical yield (α-tocopheryl acetate) 96.1%. This crude acetate is distilled in a bulb tube oven (250° C./10$^{-1}$ mbar); there are obtained 27.25 g of α-tocopheryl acetate as a slightly yellowish oil which crystallizes slowly upon standing at room temperature. α-Tocopheryl acetate content (GC, internal standard squalane) 94.7%, chemical yield 95.3%; stereochemical purity 99.6% R,R,R-α isomer (HPLC of the methyl ether derivative on Chiracel OD, n-hexane); the product is identical with α-tocopheryl acetate according to $^1$H-NMR, IR, MS and microanalytical data.

EXAMPLE 3

Hydroxymethylation-hydrogenation of a mixture of tocopherol homologues with subsequent methanolysis (one pot process); recovery of process components 25.75 g of a mixture of tocopherol homologs from natural sources [consisting of α-tocopherol 3.9%, 2.3 mmol; β-tocopherol 1.0%, 0.6 mmol; γ-tocopherol 60.6%, 37.5 mmol; δ-tocopherol 26.4%, 16.9 mmol; total tocopherols 91.9%, 57.3 mmol; determined by GC of the acetates, internal standard squalane], 100 ml of n-hexane, 30.6 g of trimethyl borate azeotrope in methanol (trimethyl borate content 70 wt.%, corresponding to 21.4 g of trimethyl borate), 10.3 g of paraformaldehyde (corresponding to 344 mmol, 6 mol equiv., based on total tocopherols), 3.1 ml of water (low in ions, 172 mmol, for the production of 57.3 mmol of boric acid, 1.0 mol equivalent based on total tocopherols) and 2.5 g of palladium on active charcoal (10%, Degussa E10N/D) are placed together in a 500 ml steel stirring autoclave having a mechanical gasification stirrer.

After closure the autoclave is pressurized to about 10 bar of hydrogen and the pressure is subsequently released. This procedure is repeated three times and then the autoclave is again pressurized to 10 bar of hydrogen and heated to 160° C. for about 30 minutes while stirring (300 r/min.). The pressure thereby rises to 23.7 bar. Further hydrogen is introduced until the pressure is 30 bar and the mixture is stirred for 5 hours at 159–160° C. and with an open hydrogen valve, with the pressure being regulated at between 30.1 and 31.2 bar. The mixture is then left to cool to 43° C. for 30 minutes, the pressure released and 80 g of methanol are introduced without opening the autoclave. The closed autoclave is heated to 162° C. for 15 minutes with stirring (the internal pressure amounts to 21.6 bar) and then left to cool to 20° C. during 15 minutes.

After opening the autoclave the reaction mixture is separated from the catalyst over a frit containing 1 g of Speedex (filter aid) and the solid residue (palladium on active charcoal) is washed with three equal portions, a total of 100 ml, of n-hexane. The combined filtrates form a two-phase mixture of 300 ml total volume which is composed of 165 ml of an upper, yellow-green hexane phase and 135 ml of a lower, colourless methanol phase. This mixture is treated with 70 ml of water, stirred vigorously for 10 minutes and separated in a separating funnel. The lower colourless phase (205 ml) contains water, methanol and boric acid and is subjected to "reactive distillation" (see Example 4) in order to recover the components.

The solvent is distilled off from the upper yellow organic phase (165 ml) at 400 mbar and a bath temperature of 60° C. (hexane recovery according to FIGS. 1 and 2 hereinafter) and the residue is dried to constant weight; 27.78 g of crude α-tocopherol as a yellow to light brown oil; content (GC of the acetates, internal standard squalane) α-tocopherol 85.9%, chemical yield (α-tocopherol) 96.7%, no other homologues (β-, γ-, δ-tocopherol), 7-hydroxymethyl-β-tocopherol 1.1%, [in a further batch 27.01 g of crude product containing 87.3% α-tocopherol are obtained, chemical yield 95.6% α-tocopherol, no other homologues (β-, γ-, δ-tocopherol), 7-hydroxymethyl-β-tocopherol 0.6%]. The crude α-tocopherol is acetylated as in Example 1: 30.18 g of crude α-tocopheryl acetate as a yellow oil; content (GC, internal standard squalane) α-tocopheryl acetate 85.6%, chemical yield α-tocopheryl acetate) 95.4%. This crude acetate is distilled in a bulb tube oven (250° C./$10^{-1}$ mbar): there are obtained 26.73 g of α-tocopheryl acetate as a slightly yellowish oil which crystallizes slowly on standing at room temperature. Content (GC, internal standard squalane) α-tocopheryl acetate 95.6%, chemical yield 94.3%; stereochemical purity: 99.5% R,R,R-α isomer (HPLC of the methyl ether derivative on Chiracel OD, hexane); the product is identical with α-tocopheryl acetate according to $^1$H-NMR, IR, MS and microanalysis.

The manufacturing process, the working-up, the recovery of the process components and their recycling for a new batch, which are described here, are presented schematically in FIG. 1 herein in which for the most part the respective chemical symbols are used and Me stands for methyl.

Figure 2:
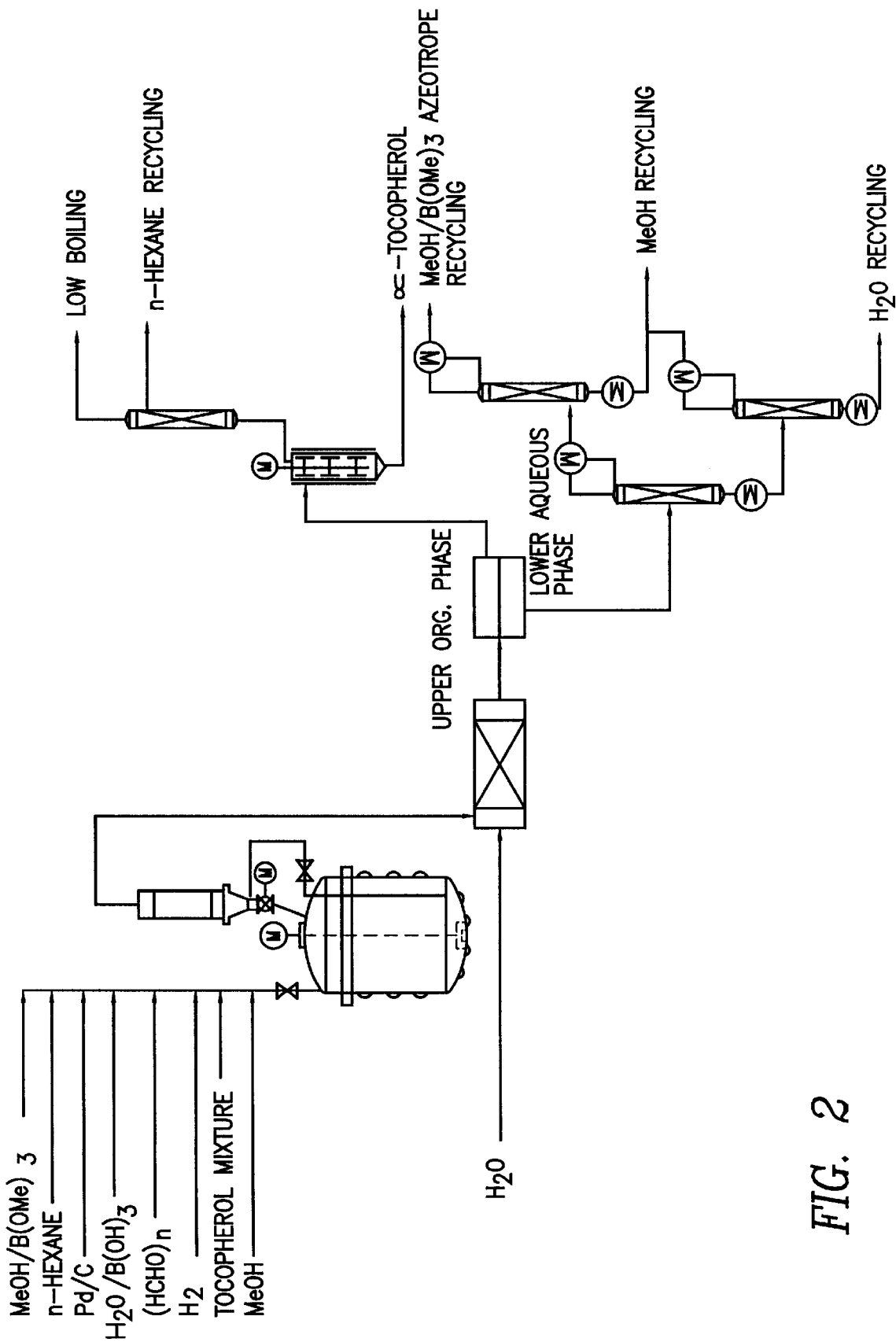
FIG. 2: A processing plant for performing the exemplified process, working-up and recovery.

FIG. 2 herein, in which likewise the respective chemical symbols are used and Me stands for methyl, shows a processing plant for performing the exemplified process, working-up and recovery.

EXAMPLE 4

Reactive distillation and recycling of the solvents and boron reagents

A glass plate column of 50 mm diameter is used to evaluate the feasibility of a continuous distillation of the solvents with concomitant conversion of the boric acid into trimethyl borate. The column has 32 usable plates and the inlet is situated in the middle of the column.

Mixtures having a representative quality are produced synthetically for all evaluations. These mixtures consist on average of 56 ma-% methanol, 9 ma-% boric acid and 35 ma-% water. The inflow stream into the column amounts to 1000 g/h and the reflux: withdrawal ratio at the column head is adjusted to 35:1. After the column has reached the stationary operational state several evaluations are carried out over a period of in each case 8 hours or 7 hours. From this there is obtained a head stream of between 240 and 242 g/hour and correspondingly a bottom stream of between 753 and 757 g/hour with an average evaluation error of 0.29%.

Analyses of the head products are effected using a GC internal standard for the methanol determination and a boric acid titration with mannitol for the trimethyl borate determination. Moreover, a density curve is produced for the entire concentration range of trimethyl borate/methanol. It is thereby possible to determine the head concentration by a simple density determination. Both methods give identical results within the bounds of analytical accuracy. The concentration of the bottom product is also determined using a GC internal standard for methanol and using a Karl-Fischer titration for water. In addition, the unreacted boric acid, which leaves the installation as the bottom product, is determined by mannitol titration.

The analytical results show that the boric acid in the column can be converted to an extent of ≧98.5% into trimethyl borate. This leaves the column as the head product with a concentration between 59.5 and 62 ma-%, and the remainder consists of methanol. A mixture consisting of about 57 ma-% of water and about 43 ma-% of methanol is obtained as the bottom product. In addition, about 0.18 ma-% of unreacted boric acid is still present.

Since the head product contains too much methanol compared with the material used in the hydroxymethylation, it must be converted into an about azeotropic composition by further rectification. This is carried out in a second glass plate column, likewise of 50 mm diameter. The column has 73 usable plates. Input is effected here at the 16th plate (counted from the top). The distillative working-up is conventional and will therefore not be explained in more detail. The head product obtained is a mixture containing 72–74 ma-% trimethyl borate and correspondingly 28–26 ma-% methanol. Methanol which is to a large extent pure can be removed as the bottom product.

The same column is likewise used to separate the methanol/water mixture which emerges as the bottom product from the reactive distillation column. This separation is also a typical standard operation in the chemical industry and does not require detailed explanation. On effecting the procedure a largely complete separation between methanol (head product) and water (bottom product) is achieved.

We claim:
1. A process for producing α-tocopherol from a non-α-tocopherol, wherein the non-α-tocopherol is free of or admixed with α-tocopherol, which process comprises reacting the non-α-tocopherol with formaldehyde or formaldehyde-producing compound in a reaction mixture which further comprises boric acid or a boric acid-producing compound and a solvent comprising an azeotropic mixture of trimethyl borate and methanol and a non-polar organic solvent wherein:
   said reaction is carried out under catalytic reducing conditions at a temperature in the range from about 130° C. to about 180° C.; and
   the mol equivalent ratio of formaldehyde to non-α-tocopherol is in a range from about 2:1 to about 10:1, the mol equivalent ratio of boric acid to total non-α-tocopherol and α-tocopherol is in a range from about 0.1:1 to about 4:1, the mol equivalent ratio of trimethyl borate to total non-α-tocopherol and α-tocopherol is in a range from about 0.1:1 to about 10:1, and the ratio of liters of non-polar organic solvent per mol equivalent of total non-α-tocopherol and α-tocopherol is in a range from about 1:1 to about 10:1;

so that the non-α-tocopherol is reacted to produce the α-tocopherol.

2. The process of claim 1 wherein the catalytic reducing conditions comprises reacting the non-α-tocopherol and the formaldehyde or formaldehyde-producing compound in the presence of sufficient quantity of a noble metal hydrogenation catalyst and under sufficient hydrogen pressure so that the non-α-tocopherol is reacted to produce the α-tocopherol.

3. The process of claim 2 wherein the boric acid-producing compound is trimethyl borate and the reaction mixture further comprises water wherein the mol equivalent ratio of water to total non-α-tocopherol and α-tocopherol is in the range from about 0.3:1 to about 12:1.

4. The process of claim 3 wherein the weight ratio of trimethyl borate to methanol in the azeotropic mixture in is a range from about 50:50 to about 75:25.

5. The process of claim 4 wherein the mol equivalent ratio of trimethyl borate to total non-α-tocopherol and α-tocopherol is in a range from about 1:1 to about 4:1.

6. The process of claim 5 wherein the non-polar organic solvent is a lower alkane, a mixture of lower alkanes or an aromatic hydrocarbon.

7. The process of claim 6 wherein the mol ratio of formaldehyde to non-α-tocopherol is in a range from about 4:1 to about 8:1.

8. The process of claim 7 wherein the non-polar organic solvent is n-hexane.

9. The process of claim 8 wherein the reaction is carried out at a temperature in a range from about 140° C. to about 170° C.

* * * * *